(12) United States Patent
Gruenwald

(10) Patent No.: US 6,214,209 B1
(45) Date of Patent: *Apr. 10, 2001

(54) METHOD OF MEASURING OXYGEN

(75) Inventor: Werner Gruenwald, Gerlingen (DE)

(73) Assignee: Robert Bosch GmbH, Stuttgart (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/986,708

(22) Filed: Dec. 8, 1997

(30) Foreign Application Priority Data

Dec. 1, 1993 (DE) .................................. 43 40 875

(51) Int. Cl.[7] .................................................. G01N 27/41
(52) U.S. Cl. ........................ 205/784.5; 204/425; 204/426
(58) Field of Search .................................. 204/421–429; 205/783.5, 784, 784.5, 785

(56) References Cited

U.S. PATENT DOCUMENTS 4,769,124 * 9/1988 Okada et al. .................... 204/426
5,397,442 * 3/1995 Wachsman ....................... 204/426
5,494,557 * 2/1996 Hotzel et al. .................... 204/426

FOREIGN PATENT DOCUMENTS

3908393 * 1/1991 (DE) .
95/30146 * 11/1995 (WO) .

* cited by examiner

*Primary Examiner*—T. Tung
(74) *Attorney, Agent, or Firm*—Michael J. Striker

(57) ABSTRACT

An oxygen measuring sensor is proposed, having a pump cell (20) with outer and inner pump electrodes (17, 19) disposed on a solid electrolyte (11) which conducts oxygen ions, of which the inner pump electrode (17) is exposed in a diffusion conduit (15) to the gas to be measured. A further electrode (18) of a measuring cell (21) is disposed in the diffusion conduit (15) behind the inner pump electrode (17) in the direction of diffusion, at which a partial oxygen pressure, which lies at least approximately in the vicinity of lambda=1, can be set by means of the pump cell (20), so that the pump cell (20) operates outside of the limiting current range of the current/voltage characteristic curve.

3 Claims, 2 Drawing Sheets

METHOD OF MEASURING OXYGEN

The invention relates to an oxygen measuring sensor in accordance with the species of the main claim. The oxygen measuring sensors of the species operate in accordance with the diffusion limiting current principle, wherein the limiting current is measured at a constant voltage applied to both electrodes of the sensor element. In an exhaust gas generated in internal combustion engines this current is a function of the oxygen concentration, as long as the diffusion of the gas to the pump electrode determines the speed of the occurring reaction. It is known, for example from DE-PS 37 28 618, to design such sensors operating in accordance with the polarographic measuring principle in such a way, that the anode as well as the cathode are exposed to the gas mixture to be measured, wherein the cathode has a diffusion barrier in order to make operating within the diffusion limiting current range possible. Such limiting current sensors are suitable for determining the lambda values in gas mixtures with excess oxygen, i.e. in lean gas mixtures.

An electrical potential of sufficient strength is applied to the electrodes of the pump cell for handing off the oxygen present between the pump electrode and the solid electrolyte in such a way, that the measured current is a function of the oxygen being diffused through the pores of the pump electrode. In accordance with the current/voltage characteristic curves of limiting current sensors, the current is independent of the applied voltage and is only determined by the concentration gradients upstream of the pump electrode, i.e. by the oxygen concentration in the gas mixture. The current/voltage characteristic curves first start with a relatively steep slope which is primarily determined by the ohmic resistance of the probe. The adjoining horizontal portion of the curve is the limiting current range, which in good probes must extend as parallel as possible in respect to the abscissa. Deviations from the parallel course of the curve are generated with higher oxygen concentrations in particular, wherein there is no longer a strict linearity between current and concentration. It depends on the strength of the diffusion resistance and the current-carrying capacity of the pump electrodes, up to which concentrations there is sufficient linearity.

ADVANTAGES OF THE INVENTION

In contrast thereto, the oxygen measuring sensor of the invention with the characterizing features of the main claim has the advantage that a linear course of the probe signal over the oxygen concentration in the gas mixture is present even at high oxygen concentrations. This results in an improved operational accuracy of the oxygen measuring sensor over the entire range of the concentrations to be measured in a lean exhaust gas. Furthermore, the response sensitivity in the course of dynamic pressure change behavior is clearly improved, which will be addressed at a later time.

Advantageous further developments of the oxygen measuring sensor of the invention are possible by means of the steps recited in the dependent claims. Pick-up of the measuring signal of the portion of the current/voltage characteristic curve which follows Ohm's law can be achieved even at high oxygen concentrations by means of the interior pump electrode extending along the diffusion direction in the diffusion conduit. The number of electrode connections can be reduced by combining the anodes of the pump cell and the measuring cell. Operation of the oxygen measuring sensor within the ohmic range of the current/voltage characteristic curve also makes it possible that merely a trimming potentiometer is sufficient for calibrating the oxygen measuring sensor.

BRIEF DESCRIPTION OF THE DRAWINGS

An exemplary embodiment of the invention is represented in the drawings and will be explained in detail in the subsequent specification.

EXEMPLARY EMBODIMENT

Figure 1:
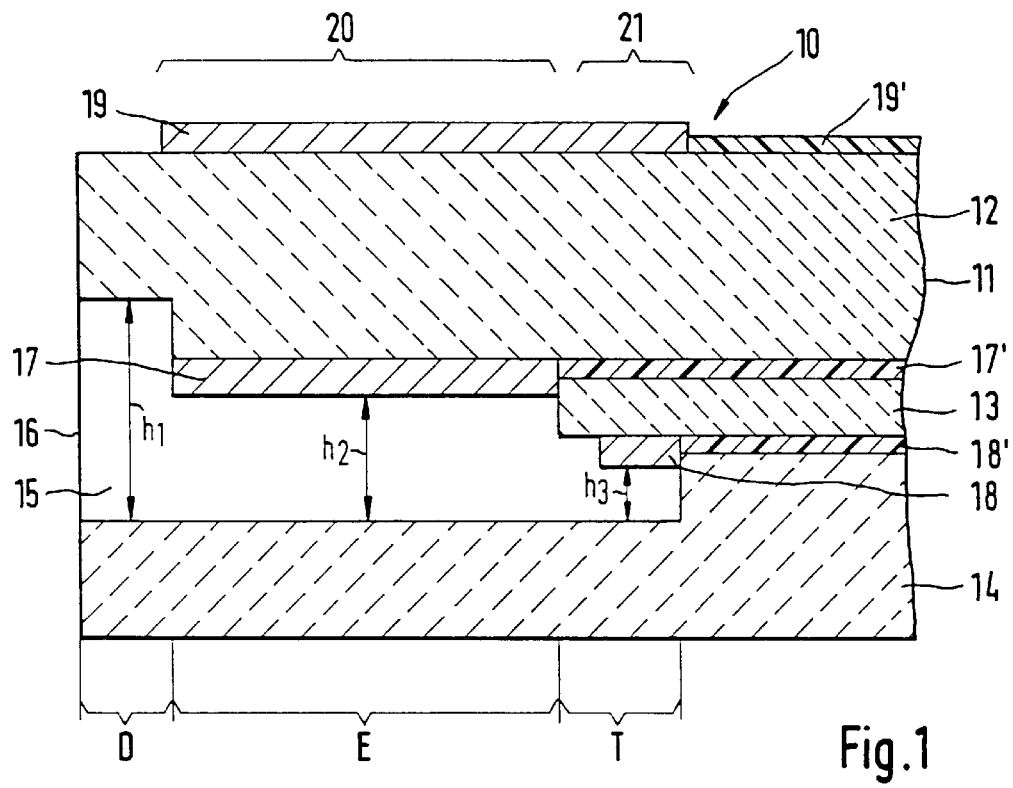
FIG. 1 shows a longitudinal sectional view through a portion of the oxygen measuring sensor located on the side of the gas to be measured.

In accordance with FIG. 1, the oxygen measuring sensor 10 has a solid electrolyte substrate 11 with a diffusion conduit 15 having a diffusion opening 16 toward the gas mixture. The solid electrolyte substrate is constructed of three solid electrolyte foils 12, 13, 14 disposed above each other, for example. The diffusion conduit 15 is constructed to be stepped in the diffusion direction and has a diffusion segment D of a diffusion segment height $h_1$, a pump segment E of a pump segment height $h_2$ and a testing chamber T of a testing chamber height $h_3$, wherein the diffusion segment height $h_1$ is greater than the pump segment height $h_2$, and the pump segment height $h_2$ in turn is greater than the testing chamber height $h_3$. However, embodiments are also possible, wherein the diffusion segment height $h_1$ and the pump segment height $h_2$, or all three heights $h_1$, $h_2$ and $h_3$ are of the same height. It is also conceivable to omit the diffusion segment D.

An inner pump electrode 17, wired as a cathode, is disposed in the diffusion conduit 15 in the area of the pump segment E. A test electrode 18 is positioned in the diffusion direction behind the inner pump electrode 17 in the testing chamber T. An outer pump electrode 19 wired as an anode and also subjected to the gas mixture is provided outside of the diffusion conduit 15 on the solid electrolyte substrate 11 and located opposite the pump electrode 17 and the test electrode 18. Strip conductors 17', 18' and 19' are respectively located between the solid electrolyte foils 12, 13 and 14 and are brought to the respective electrodes 17, 18 and 19 and to customary connections, not shown. The strip conductors 17', 18' and 19' are suitably electrically insulated in respect to the solid electrolyte foils 12, 13, 14 by means of insulating layers, not shown.

The inner pump electrode 17 and the outer pump electrode 19 constitute a pump cell 20, and the test electrode 18 together with the outer pump electrode 19 a measuring cell 21. However, it is also conceivable in the same way to dispose the second electrode of the measuring cell 21 separately from the pump electrode 19. In this embodiment it is furthermore conceivable to dispose this second electrode with an additional reference conduit and to expose it to a reference gas. In this case it is possible to realize an oxygen measuring sensor which is suitable for measuring the oxygen concentration from a lean to a rich exhaust gas.

Figure 3:
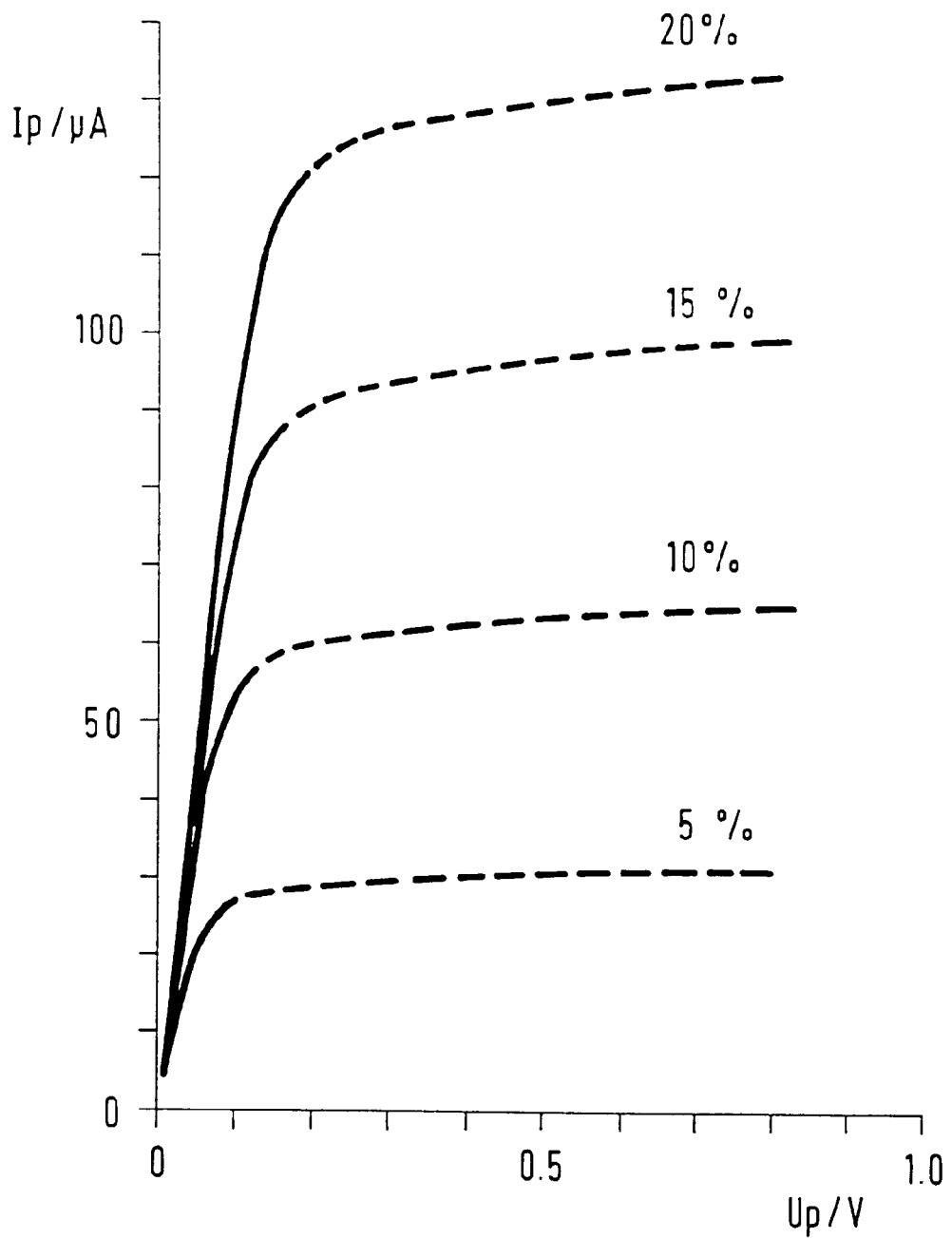
FIG. 3 shows the current/voltage characteristic curve of a limiting current probe.

The current/voltage characteristic curves of an oxygen measuring sensor operating in accordance with the limiting current principle can be seen in FIG. 3 at various oxygen concentrations. The relatively steep course present at low voltage values $U_p$ is primarily determined by the ohmic resistance and the polarization of the electrodes of the oxygen measuring sensor. The adjoining portion of the curves, represented by dashed lines, is the limiting current range which, as already mentioned at the outset, no longer extends parallel in respect to the abscissa, in particular at higher concentrations, so that therefore no strict linearity between the current $I_p$ and the concentration exists. The portion of the characteristic curves obeying Ohm's law, however, extends linearly at low voltage values $U_p$. The oxygen measuring sensor of the invention uses this ohmic range of the characteristic curve for detecting a measurement signal, wherein the pump current $I_p$ is also used as a measuring signal in an advantageous manner. However, it is also conceivable to use the pump voltage $U_p$ as the measurement signal on the basis of Ohm's law.

Based on a catalytic reaction, known per se, the oxygen is pumped over the inner pump electrode 17, which extends flat in the diffusion direction, via an oxygen ion line through the solid electrolyte substrate 11 to the outer pump electrode 19 and there is released again into the gas mixture. In this case the pump current $I_p$ of the pump cell 20 is adjusted in such a way a partial oxygen pressure of $10^{-10}$ to $10^{-12}$ bar is present at the test electrode 18 in the test chamber T, which corresponds to lambda=1. If, for example, the measuring cell 21 is wired as the second pump cell, the adjustable concentration range at lambda=1 is detected because the pump current in this area between the electrode 18 and the outer pump electrode 19 is zero.

In connection with the already discussed embodiment wherein the measuring cell 21 is wired as a Nernst cell with a reference electrode exposed to a reference gas, the electromotive force of, for example 450 mV, is received as the signal for the range lambda=1. By means of this embodiment it is possible to design the oxygen measuring sensor as a broadband sensor, wherein each time lambda=1 has been reached, a pole reversal of the pump cell 20 takes place so that, as described, either oxygen is pumped out of the diffusion conduit 15 in case of lean exhaust gas or, in case of rich exhaust gas, oxygen is pumped into the diffusion conduit 15. An anodic pump current is measured in case of the latter pumping direction as the sensor signal, which is also located in the ohmic range.

Figure 2:
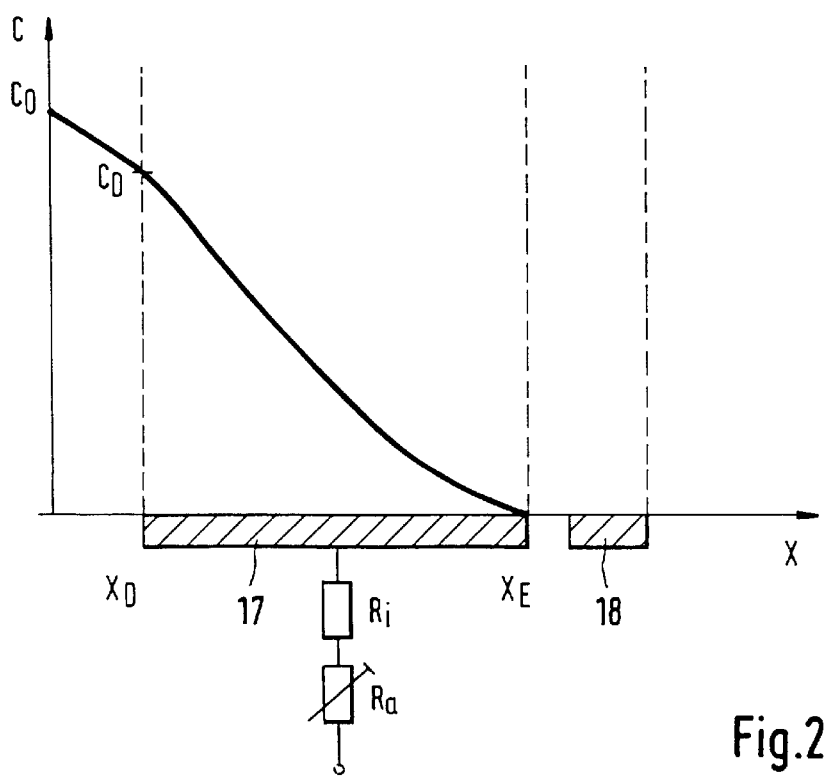
FIG. 2 shows the course of the oxygen concentration along the diffusion conduit of the oxygen measuring sensor of FIG. 1.

The course of the oxygen concentration C via the diffusion segment X in the diffusion conduit 15 can be seen in FIG. 2. In accordance with this, the oxygen concentration $C_O$ decreases linearly from the diffusion conduit opening 16 to the start of the pump segment E down to the concentration $C_D$. The start of the pump segment E is identified by the diffusion segment $X_D$. The oxygen concentration C extends in a parabola shape within the pump segment to the end of the pump segment E identified by $X_E$. At the point $X_E$ the oxygen concentration C has reach the range lambda=1 at a partial oxygen pressure of $10^{-10}$ to $10^{-12}$ bar. The same partial oxygen pressure is present at the test electrode 18 in the test chamber T.

The course of the concentration in the pump segment E can be described by the following function:

$$C(x) = \frac{j}{z \cdot F \cdot D \cdot h_2}\left(\frac{x^2}{2} - X \cdot X_E + \frac{X_E^2}{2}\right) \quad (1)$$

wherein z=4 (valence of the oxygen in accordance with the cathodic reaction)

$$4e + O_2 \rightarrow 2O^{2-} \quad (2)$$

F=Faraday number=96 400 A s/mol
D=Diffusion coefficient
j=pump current density=i/(b·e)
  with total pump current i, b=width of the pump segment,
  e=length of the pump segment.
The connection $$C = \frac{i}{z \cdot F \cdot D \cdot b}\left(\frac{E}{2h_2} - \frac{D}{h_1}\right) \quad (3)$$

results for the oxygen concentration C in the gas mixture with the pump current $I_p$ in the adjusted state.

In connection with equation (3) it should be stressed that the pump electrode 17 does not operate in the limiting current range, so that therefore Ohm's law $$I_p = U_p/R \quad (4)$$

applies to $I_p$, wherein
  $U_p$=pump voltage applied,
  $I_p$=pump current of the pump cell 20,
  R=resistance of the pump circuit, composed of the resistance $R_i$ of the pump cell and an exterior trimming resistance $R_a$:

$$R = R_i + R_a$$

Therefore, the following results from Equation (3):

$$C = \frac{U_p}{R_i + R_a} \cdot \frac{\frac{X_E}{2h_2} - \frac{D}{h_1}}{z \cdot F \cdot D \cdot b} \quad (5)$$

It becomes clear from Equation (5) that an exact linear correlation ensues between the oxygen concentration C and the appearing pump voltage $U_p$. The proportionality factor contains the geometric values $(X_E/2h_2 - D/h_1)/b$ and $R_i$, which are subjected to corresponding manufacturing variations. The trimming potentiometer $R_a$ represented in a replacement circuit diagram in FIG. 2, is used to calibrate the oxygen measuring sensor and sets the proportionality factor to a constant value. The linear connection between the oxygen concentration C and the pump voltage $U_p$ in accordance with equation (5) simultaneously means a linear connection between the oxygen concentration C and the pump current $I_p$.

In the course of operating the oxygen measuring sensor, reaching the oxygen concentration at lambda=1 is now detected by means of the test electrode 18 by a control circuit, not shown. When lambda=1 has been reached, the pump current $I_p$ flowing through the pump cell 20 is measured by the control circuit and appropriately evaluated. In contrast to customary limiting current probes in this case the pump voltage $U_p$ is not further increased in such a way that the pump cell 20 comes into the limiting current range, shown as a dashed line in FIG. 3. It the test electrode 18 has been set to a partial oxygen pressure for lambda=1, the end $X_E$ of the flat-shaped pump-electrode 17 also lies at least in the vicinity of this concentration. The concentration continues to increase toward the diffusion opening 16 in accordance with FIG. 2. Because of this, in the extreme case, limiting current conditions at the pump electrode 17 are present only at the end $X_E$ of the pump electrode 17. The pump current $I_p$, measured over the entire electrode surface of the pump electrode 17, however, does not reach the limiting current range and therefore remains within the ohmic range of the characteristic curve in accordance with FIG. 3. If the oxygen measuring sensor in used in rich exhaust gas, the course of the concentration in accordance with FIG. 2 applies for the gas components which can be oxidized, such as CO and $NO_x$, for example.

What is claimed is:

1. A method of measuring an oxygen concentration in gas mixtures of exhaust gasses of internal combustion engines, the method comprising the steps of providing a pump cell with an outer pump electrode and an inner pump electrode; applying a pump voltage $U^p$ at the electrodes so as to provide a pump current forming a measuring signal; arranging a further electrode of a measuring cell in a diffusion conduit behind the inner pump electrode as considered in a diffusion direction; forming the diffusion conduit as a diffusion conduit which is stepped in the diffusion direction and is provided with a diffusion segment with a diffusion segment height, a pump segment with a pump segment height, and a testing chamber with a testing chamber height, so that the diffusion segment height is greater than the pump segment height and the pump segment height is greater than the testing chamber height; suitably selecting the pump voltage at the pump cell so as to set at the further electrode of the measuring cell a partial oxygen pressure of at least approximately lambda=1, to thereby form the pump current $I_p$ which forms the measuring signal in accordance with $I_p = U_p/R$, wherein R is an electrical resistance of the pump cell, so that the pump cell operates outside a limiting current range.

2. A method as defined in claim 1; and further comprising the step of operating the measuring cell as a Nernst cell with an electromotive force provided for an oxygen partial pressure of lambda=1.

3. A method as defined in claim 1; and further comprising the step of operating the measuring cell as a pump cell; and setting the pump current for an oxygen partial pressure of lambda=1.

* * * * *